United States Patent
Saxena et al.

(10) Patent No.: US 7,598,415 B2
(45) Date of Patent: Oct. 6, 2009

(54) PROCESS FOR THE PREPARATION OF P-TOLUIC ACID BY LIQUID PHASE OXIDATION OF P-XYLENE IN WATER

(75) Inventors: Mahendra Pratap Saxena, Uttaranchal (IN); Ashok Kumar Gupta, Uttaranchal (IN); Satish Kumar Sharma, Uttaranchal (IN); Dinesh Prasad Bangwal, Uttaranchal (IN); Krishan Kumar, Uttaranchal (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 11/378,055

(22) Filed: Mar. 17, 2006

(65) Prior Publication Data

US 2006/0247464 A1    Nov. 2, 2006

(51) Int. Cl.
*C07C 51/265* (2006.01)
(52) U.S. Cl. .................... 562/412; 562/414
(58) Field of Classification Search .......... 562/412, 562/414
See application file for complete search history.

(56) References Cited

U.S. PATENT DOCUMENTS

| 2,833,816 | A | 5/1958 | Alfred et al. |
| 3,046,305 | A | 7/1962 | Braunwarth |
| 3,064,044 | A | 11/1962 | Baldwin |
| 4,259,522 | A | 3/1981 | Hanotier |
| 4,334,086 | A | 6/1982 | Hanotier et al. |
| 4,357,475 | A | 11/1982 | Hanotier et al. |

OTHER PUBLICATIONS

Sayed Akhtar H. Zaidi, "Liquid Phase Oxidation of P-xylene to P-toluic Acid," Applied Catalysis, vol. 27, (1986) pp. 99-106, Elsevier Science Publishers B. V., Amsterdam.

*Primary Examiner*—Paul A Zucker
*Assistant Examiner*—Yevegeny Valenrod
(74) *Attorney, Agent, or Firm*—Luedeka, Neely & Graham, PC

(57) ABSTRACT

The present invention provides a process for the preparation of p-toluic acid by liquid phase oxidation of p-xylene using oxygen or air as oxidant in the presence of p-toluic acid, water as solvent and cobalt salt or its combinations with salts of Ce, Mn as catalyst. Oxidation is carried out at 130-190° C. and pressure sufficient to keep water in liquid state. Oxidation step is followed by filteration to obtain p-toluic acid as major product. Untreated p-xylene is recovered and recycled and the catalyst is recovered from aqueous phase and is recycled.

19 Claims, No Drawings

PROCESS FOR THE PREPARATION OF P-TOLUIC ACID BY LIQUID PHASE OXIDATION OF P-XYLENE IN WATER

FIELD OF THE INVENTION

The present invention relates to a process for preparation of p-toluic acid by liquid phase oxidation of p-xylene in water.

Particularly this invention relates to the process of preparation of p-toluic acid by liquid phase oxidation of p-xylene in water in the presence of p-toluic acid and cobaltous acetate or its combination with cerium(III)acetate as catalyst and a catalyst consisting of a cobalt salt or its combination with salt of cerium and or Manganese. More particularly this invention relates to a process for preparing p-toluic acid by oxidation of p-xylene in water as solvent.

BACKGROUND OF THE INVENTION p-Toluic acid is an important chemical intermediate, which is widely used to prepare finished products in the manufacture of medicines, agro-chemicals, dyestuffs, optical brighteners etc. It is also used in organic synthesis of various chemical compounds. p-Toluic acid is produced as by- product during the production of tere-phthalic acid/dimethyl tere-phthalate, which are mainly produced by liquid phase oxidation of p-xylene by oxygen/air in acetic acid medium.

Oxidation of p-xylene to tere-phthalic acid in acetic acid solvent in the presence of bromine or bromine containing compound as initiator and a catalyst containing cobalt and manganese components has been disclosed in U.S. Pat. No. 2,833,816 and is practiced world over. Homogeneous catalyst system consisting of cobalt, manganese and bromide is the heart of this process. Oxygen compressed in air is used an oxidant and acetic acid as solvent.

Although the use of bromine is advantageous for such liquid phase oxidation, but its use is associated with some drawbacks. The highly corrosive bromine acetic acid water environment during oxidation require the use of costly titanium lined equipments in some part of the process. Additionally, during reaction bromine also produce methyl bromide, which is hazardous gas. Moreover, in the bromine promoted process, the reaction mixture must be maintained "Substantially anhydrous" (U.S. Pat. No. 3,064,044).

Another patent (U.S. Pat. No. 3,046,305) described a process for the preparation of p-toluic acid starting from toluene, wherein toluene is reacted with chloroformamide under the conditions of Friedel and Craft reaction, and the product thus obtained is hydrolysed to p-toluic acid. This process is not in practice.

There are other patents which report oxidation of p-xylene to terephthalic acid in the presence of water. Patent (U.S. Pat. No. 4,334,086) assigned to Labofina, S. A., Belgium describes a two stage process for oxidation of p-xylene at the 170° C. in the presence of Co—Mn catalyst and 10% (wt %) water in first stage. In second stage partially oxidized compounds are further oxidized at 200° C. in the presence of 20-70% water. After the oxidation, water soluble compounds are separated from insoluble terephthalic acid at 180-200° C., which include p-toluic acid, catalyst and other by products, which are recycled for further oxidation. Crude terephthalic acid crystals obtained in sedimentation column still have about 4.5% p-toluic acid and 2.5% 4-carboxybenzaldehyde as impurities. Labofina. S. A., (U.S. Pat. No. 4,357,475) also described a correlation between temperature of sedimentation column and the oxidation temperature for similar process of oxidation of p-xylene in the presence of water as described above. Labofina. S. A., (U.S. Pat. No. 4,259,522) also described similar process for iosphthalic acid by oxidizing m-xylene in the presence of water. Most of the patents, including above mentioned patents describe the processes for the oxidation of p-xylene to produce tere-phthalic acid as the main product. Little or scanty information is available for the processes to selectively produce p-toluic acid, by liquid phase oxidation of p-xylene in aqueous medium. Studies on oxidation of p-xylene to p-toluic in acetic acid medium in presence of bromide initiator has been described by S. H. Zaidi [Applied Catalysis, 27, 99-106 (1986)]. Therefore, a process to produce p-toluic acid as main product by liquid phase oxidation of p-xylene in water under mild operating condition without using bromine compounds as initiator would not only be of a great economic and commercial potential, but also be an environment friendly technology.

OBJECTIVES OF THE INVENTION

The main object of the present invention is to provide a process for preparation of p-toluic acid by liquid phase oxidation of p-xylene in water.

Another object of the present invention is to provide a process for carrying out oxidation of p-xylene in the presence of ecofriendly solvents such as water and bromine free catalysts thereby avoiding the use of corrosive substances such as alkanoic acid as solvent and bromine compound as initiator.

Yet another object of the present invention is to provide a process wherein the by-products of the reaction such as terephthalic acid and carboxybenzaldehyde are produced in minimum possible amount so that p-toluic acid is obtained in high purity. Yet another object of the present invention is to provide a process for producing p-toluic acid by oxidizing p-xylene with oxygen or air or $N_2$—$O_2$ mixture in the presence p-toluic acid and water.

SUMMARY OF THE INVENTION

Accordingly the present invention provides a process for preparation of p-toluic acid by liquid phase oxidation of p-xylene in water which comprises oxidizing p-xylene or a mixture of p-xylene and p-toluic acid with oxygen, air or oxygen/nitrogen mixture, at a pressure of 3-25 $Kg/cm^2$ with an exit flow rate of 60-80 ml/min, in the presence of catalytically active salt of transition metal selected from the group consisting of Co, Mn, Ce and combination thereof in the range 1-200 mmol per mole of p-xylene in water in the range of 40-85% of total charge, at a temperature ranging between 130-190° C., for a period of 5-10 hrs, cooling the above said reaction mixture and removing the un reacted p-xylene by washing with an organic solvent, followed by filtration to obtain the desired product.

In an embodiment of the present invention the amount of catalyst used is 5-160 mmol per mole of p-xylene.

In another embodiment the transition metal salt used is selected from the group consisting of cobaltous acetate, manganese acetate, cerium acetate and a combination thereof.

In yet another embodiment the cobaltous acetate used is 5-150 mmol per mole of p-xylene.

In yet another embodiment the concentration of cerium (III) acetate used is a maximum of 6 mmol per mole of p-xylene.

In yet another embodiment the p-toluic acid used comprises of about 0.1 to about 1.5 mmol per mole of p-xylene.

In yet another embodiment water comprises of about 50 to about 80 weight percent of the reaction mixture.

In yet another embodiment pressure is sufficient to keep water in liquid phase preferably in the range 5to 20 kg/cm².

In yet another embodiment, the reaction mixture is substantially free from extraneous organic solvent.

In yet another embodiment reaction products are recovered by filtration, followed by distillation of filtrate and washings to recover unreacted p-xylene and a part of solvent(water).

In yet another embodiment the remaining water in the products consisting small amount of reaction products and catalyst is recycled in subsequent oxidation.

In still another embodiment of the present invention remaining water in the products consisting small amount of reaction products and catalyst is recycled in subsequent oxidation.

DETAIL DESCRIPTION OF THE INVENTION

The said process is carried out in a stirred reactor, in aqueous solution containing 50-80% weight percent of water at a temperature between 130-190° C. and under 5-20 kg/cm² pressure, sufficient to maintain water in liquid state, in the presence of catalytically active metal compound selected from Mn, Ce and its mixture with cobalt compound. After the reaction, product is separated out as solid product by filtration. Unreacted p-xylene is recovered from the filtrate by distillation and recycled. Remaining aqueous solution containing small amount of reaction products and catalyst is recycled in subsequent oxidation.

Various processes have been described in the literature for production of terephthalic acid by liquid phase oxidation of p-xylene in acetic acid solvent in the presence Co/Mn catalysts and bromine containing compound as initiator. Although, effect of water as diluent has also been reported by Hanotier et. al. (U.S. Pat. Nos. 4,334,086 & 4,357,475) in such processes, but little information is available on oxidation of p-xylene by molecular oxygen in aqueous medium to produce p-toluic acid as major project.

The oxidation reaction is carried out wherein the catalyst is selected from compounds of Co, Mn in combination or without cerium; the concentration of catalyst being in the range 1-200 mmol per mole of p-xylene. The compounds of cobalt and manganese are preferably cobaltous acetate and manganous acetate; the concentration of cobaltous acetate being in the range 5-150 mmol per mole of p-xylene. The compound of cerium is cerium (III) acetate.

In the said process presence of p-toluic acid is crucial and plays a significant role during oxidation of p-xylene in water. During the investigations it was found that at 130° C., 16.6% p-toluic acid of p-xylene resulted in maximum conversion of xylene (76.87%) with 80.03%, 16-79% selectivities to p-toluic acid and terephthalic acid respectively. Presence of p-toluic acid is essential to oxidize p-xylene in water and minimum of 16.6% of p-xylene is required to get maximum conversion of p-xylene into the oxygenated products. In the process of the present invention, the concentration of p-toluic acid is in the range of about 0.1 to about 1.5 mmol per mole of p-xylene.

In the present invention the oxidation is carried out in presence of water as solvent. Presence of water as solvents makes a three phase system for the oxidation making the reaction more difficult. The present invention reveals that 55-80% water as solvent can be conveniently used for the oxidation at 130-150° C. When lower amount of water was used i.e. less than 55% of reaction mixture, the reaction mixture became a thick slurry, difficult to stir and proper mixing of reactants could not be achieved even with mechanical stirring. Poor mixing of reactants led to lower conversion of p-xylene probably due to increased resistance to diffusion of $O_2$ into liquid phase. Although, conversion of p-xylene, as well as selectivity to terephthalic acid increases to some extent with increase in temperature from 130° C. to 150° C., but selectivity to p-toluic acid remains almost the same.

In the present invention Cerium (III) acetate when used as co-catalyst in combination with cobaltous acetate in the concentration upto 6 mmol per mole of p-xylene increased the selectivity of p-toluic acid. The presence of cerium(III)acetate with cobalt(II)acetate plays a significant role during oxidation. Cerium(III)acetate when used with cobalt(II)acetate [~5% (mol %) of Co(II)] as catalyst and p-xylene was oxidized in water (77% of the charge) at 130° C. temperature and 20 kg/cm² pressure of oxygen in the presence of this catalyst [6.7% (mol %)] of p-xylene, the selectivity of p-toluic acid was increased from 77.53% to 84.68%.

In present invention the reactor contents are cooled, filtered and washed with water. The filtrate and washings are distilled, wherein, unreacted p-xylene and same part of water are distilled off as azeotropic mixture of p-xylene and water. p-Xylene thus obtained is recycled. Residual aqueous solution containing catalyst and small amount of oxidation products is also recycled in subsequent oxidation.

The present invention will be described in more detail with reference to the following examples, wherein different process conditions/reaction parameters are given for the sake of illustration only and should not be considered as limiting the scope of the invention.

EXAMPLE 1 p-Xylene, (30 g), p-toluic acid (5.0 g), cobaltous acetate (5.0 g) and water (150 g) were charged in an autoclave. This reactor was then pressurized with oxygen to about 15 kg/cm² pressure and heated to 130° C. The pressure of the reactor was maintained at 20 kg/cm² with continuous stirring and exit oxygen flow rate at 75 ml/min. After 6 hr of reaction, the reactor was cooled, the contents were filtered and washed with toluene. Total unreacted p-xylene was determined from organic phase and content of a toluene trap (kept after the reactor where through exit gases passed during the reaction) by analyzing these by gas chromatography. Solid product was also analysed by G.C. Analysis of reaction products/stream indicated 65.41% conversion of p-xylene into oxygenated products (mole %) as p-toluic acid (p-TA), 82.39%, 4-carboxybenzaldehyde (4-CBA) 1.82%, terephthalic acid (TPA), 13.50% and others 1.35%.

EXAMPLE 2 p-Xylene (30.0 g), was oxidized with oxygen at 150° C. in the presence of 5.0 g p-TA, 5.0 g cobaltous acetate and 150 g water. The reaction was carried out as in Example-1. 78.23% Of p-xylene was converted into p-TA, 90.56%; 4-CBA, 2.75%; TPA, 6.32% and others 0.30%.

EXAMPLE 3 p-Xylene (30.0 g) was oxidized with oxygen at 150° C. in the presence of 5.0 g cobaltous acetate as catalyst and 150 g of water. The reaction was carried out and processed as in Example-1. In the absence of p-TA, oxidation did not take place and almost all of p-xylene was recovered unreacted.

EXAMPLE 4 p-Xylene (30.01 g) was oxidized with oxygen at 150° C. in the presence of 4.4 g cobaltous acetate and 0.3 g cerium(III)

acetate as catalyst in 150 g of water. The reaction was carried out and worked up as in example-1. In the absence of p-TA but in the presence of cerium with cobalt. 20.05% Of p-xylene was converted into oxygenated compounds. White solid product was found consisting of p-TA 96.62% terephthalic acid 0.42% and others 2.96%.

EXAMPLE 5 p-Xylene (30.0 g) was oxidized with molecular oxygen at 130° C. in the presence of 10.04 g p-TA, 5.0 g of cobaltous acetate as catalyst and 150 g of water as solvent. The reaction was carried out and worked up as in example-1. 72.2% Of p-xylene was converted into oxygenated compounds as p-TA, 77.53%, 4CBA, 4.75%, TPA, 16.98% and others 0.73%.

EXAMPLE 6 p-Xylene (30.0 g) was oxidized with molecular oxygen at 130° C., under the experimental conditions mentioned in example-5 except that a mixture of 0.31 g of cerous acetate and 4.48 g of cobaltous acetate was used as catalyst. 67.34% Of p-xylene got converted into oxygenated compounds as p-TA, 84.68%, 4-CBA, 2.04% and TPA, 13.22%.

EXAMPLE 7 p-Xylene (30.0 g) was oxidized with oxygen at 130° C. in the presence of 10.0 g p-TA, 5.0 g of cobaltous acetate as catalyst and 150 g water as solvent. Reaction was carried out at 10 kg/cm$^2$ pressure and worked up as in example-1. 73.38% Of p-xylene was converted into oxygenated compounds as p-TA, 82.88%, 4-CBA, 2.87% and TPA, 14.25%.

EXAMPLE 8 p-Xylene (30.0 g) was oxidized with oxygen at 130° C. in the presence of 5.0 g of p-TA, 5.02 g of cobaltous acetate and 50 g of water as solvent. Reaction was carried out at 20 kg/cm$^2$ pressure and worked up as in example-1. 67.46% Of p-xylene was converted into oxygenated compounds as p-TA, 78.99%; 4-CBA, 1.46%; TPA, 16.24% and others 3.3%.

THE MAIN ADVANTAGES OF THE PRESENT INVENTION ARE

The followings are the advantages of the process for the preparation of p-toluic acid by liquid phase oxidation of p-xylene in aqueous medium.
1. The most important advantage of the process is the use of water as solvent, which is very much safe, non flammable, non toxic, easily available and cheap.
2. Quick heat transfer from the reactor during exothermic oxidation reaction in aqueous medium make the process safe.
3. Bromine free catalyst and exclusion of acetic acid solvent make the process non-corrosive. Thus no special or costly equipment is required.
4. Higher conversion of p-xylene and higher yield of p-toluic acid are comparable with those using acetic acid as solvent.

We claim:
1. A process for preparation and isolation of p-toluic acid by a single step liquid phase oxidation reaction of p-xylene in water which comprises oxidizing p-xylene or a mixture of p-xylene and p-toluic acid with oxygen, air, or an oxygen/nitrogen mixture, at a pressure of 3-25 Kg/cm$^2$ with an exit flow rate of 60-80 ml/min, in the presence of a catalytically active bromine-free salt of a transition metal selected from the group consisting of Co, Mn, Ce and combinations thereof in the range 5-160 mmol per mole of p-xylene in water in the range of 40-85 weight % of water based on a total weight of reaction mixture, at a temperature ranging between 130-150° C., for a period of 5-10 hrs, cooling the reaction mixture, removing any un-reacted p-xylene by washing the reaction mixture with an organic solvent, and filtering the reaction mixture to obtain the p-toluic acid as a desired product in a major amount and terephthalic acid in a minor amount.

2. A process according to claim 1, wherein the transition metal salt used is selected from the group consisting of cobaltous acetate, manganese acetate, cerium acetate and a combination thereof.

3. A process according to claim 1, wherein the amount of cobaltous acetate used is 5-150 mmol per mole of p-xylene.

4. A process according to claim 1, wherein the concentration of cerium (III) acetate used is a maximum of 6 mmol per mole of p-xylene.

5. A process according to claim 1, wherein p-toluic acid used comprises of about 100 to about 300 mmol per mole of p-xylene.

6. A process according to claim 1, wherein water comprises from about 50 to about 80 weight percent of the reaction mixture.

7. A process according to claim 1, wherein the pressure is preferably in the range of 5 to 20 kg/cm$^2$.

8. A process according to claim 1, wherein the reaction mixture is substantially free from extraneous organic solvent.

9. A process according to claim 1, wherein reaction products are recovered by filtration, followed by distillation of filtrate and washings to recover unreacted p-xylene and a part of solvent(water).

10. A process according to claim 1, wherein remaining water in the products consisting of a small amount of reaction products and catalyst is recycled in a subsequent oxidation reaction.

11. A process according to claim 2, wherein the concentration of cerium (III) acetate used is a maximum of 6 mmol per mole of p-xylene.

12. A process according to claim 3, wherein the concentration of cerium (III) acetate used is a maximum of 6 mmol per mole of p-xylene.

13. A process according to claim 2, wherein the amount of p-toluic acid used comprises about 100 to about 300 mmol of p-toluic acid per mole of p-xylene.

14. A process according to claim 3, wherein the amount of p-toluic acid used comprises about 100 to about 300 mmol of p-toluic acid per mole of p-xylene.

15. A process according to claim 4, wherein the amount of p-toluic acid used comprises of about 100 to about 300 mmol of p-toluic acid per mole of p-xylene.

16. A process according to claim 6, wherein pressure is preferably in the range 5 to 20 kg/cm$^2$.

17. A process for the preparation and isolation of p-toluic acid, the process consisting essentially of the steps of:
  oxidizing a reaction mixture, wherein the reaction mixture is selected from the group consisting of p-xylene and a mixture of p-xylene and p-toluic acid, with an oxidant selected from the group consisting of oxygen, air, a nitrogen/oxygen mixture, and combinations thereof, wherein said oxidation occurs in the presence of a catalytically active bromine-free salt of a transition metal selected from the group consisting of Co, Mn, Ce, and combinations thereof, in the range about 5 to about 160 mmol per mole of p-xylene in the reaction mixture, said reaction mixture further including water in the range of about 40 to about 85 weight % of water, based on a total weight of the reaction mixture, wherein the oxidation occurs at a temperature ranging between about 130° C. to about 150 ° C.;

cooling the reaction mixture;

removing the un-reacted p-xylene by contacting the reaction mixture with an organic solvent; and filtering the reaction mixture to obtain the p-toluic acid as a desired product, wherein the desired product, as made, is p-toluic acid in a major amount and relatively high purity with minimum amounts of terephthalic acid, carboxybenzaldehyde, and combinations thereof.

18. A process according to claim 17, wherein the amount of p-toluic acid used comprises about 100 to about 300 mmol of p-toluic acid per mole of p-xylene.

19. A process according to claim 17, wherein the transition metal salt used is selected from the group consisting of cobaltous acetate, manganese acetate, cerium acetate and a combination thereof.

* * * * *